United States Patent
Pilly et al.

(10) Patent No.: US 10,307,592 B1
(45) Date of Patent: Jun. 4, 2019

(54) METHOD AND SYSTEM TO ACCELERATE CONSOLIDATION OF SPECIFIC MEMORIES USING TRANSCRANIAL STIMULATION

(71) Applicant: HRL Laboratories, LLC, Malibu, CA (US)

(72) Inventors: Praveen K. Pilly, West Hills, CA (US); Michael D. Howard, Westlake Village, CA (US); Jaehoon Choe, Agoura Hills, CA (US); Rajan Bhattacharyya, Sherman Oaks, CA (US)

(73) Assignee: HRL Laboratories, LLC, Malibu, CA (US)

(*) Notice: Subject to any disclaimer, the term of this patent is extended or adjusted under 35 U.S.C. 154(b) by 252 days.

(21) Appl. No.: 15/332,787

(22) Filed: Oct. 24, 2016

Related U.S. Application Data

(60) Provisional application No. 62/245,730, filed on Oct. 23, 2015.

(51) Int. Cl.
| | | |
|---|---|---|
| *A61N 1/36* | (2006.01) | |
| *A61B 5/0476* | (2006.01) | |
| *A61B 5/00* | (2006.01) | |
| *A61N 1/20* | (2006.01) | |

(52) U.S. Cl.
CPC ........ *A61N 1/36025* (2013.01); *A61B 5/0476* (2013.01); *A61B 5/4812* (2013.01); *A61B 5/4836* (2013.01); *A61N 1/20* (2013.01)

(58) Field of Classification Search
CPC .... A61N 1/36025; A61N 1/20; A61B 5/0476; A61B 5/4836; A61B 5/4812
See application file for complete search history.

(56) References Cited

PUBLICATIONS

Marshall L, Helgadóttir H, Mölle M, Born J. Boosting slow oscillations during sleep potentiates memory. Nature. 2006; 444(7119): pp. 610-613.

Rudoy JD, Voss JL, Westerberg CE, Paller KA. Strengthening Individual Memories by Reactivating Them During Sleep. Science. Nov. 20, 2009;326(5956): pp. 1079-1079.

Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.

Rasch BH, Born J, Gais S. Combined blockade of cholinergic receptors shifts the brain from stimulus encoding to memory consolidation. J Cogn Neurosci. May 2006; 18(5): pp. 793-802.

(Continued)

*Primary Examiner* — Rex R Holmes
(74) *Attorney, Agent, or Firm* — Tope-McKay & Associates

(57) ABSTRACT

Described is a system for consolidation of specific memories of events. A sleep state detector assesses a subject's sleep state from neural recordings obtained from a high-density electroencephalogram (HD-EEG) device. During a memory encoding phase, a high-definition transcranial current stimulation (HD-tCS) system simultaneously applies a spatiotemporal amplitude-modulated pattern (STAMP) tag and a transcranial direct current stimulation (tDCS) signal to the subject as an event is experienced by the subject. During a memory consolidation phase, the HD-tCS system applies a transcranial alternating current stimulation (tACS) signal to the subject during a sleep or quiet waking state of the subject.

13 Claims, 12 Drawing Sheets

(56) References Cited

PUBLICATIONS

Gais S, Born J. Low acetylcholine during slow-wave sleep is critical for declarative memory consolidation. Proc Natl Acad Sci U S A. Feb. 17, 2004; 101(7): pp. 2140-2144.

Rasch B, Buchel C, Gais S, Born J. Odor cues during slow-wave sleep prompt declarative memory consolidation. Science. 2007; 315(5817): pp. 1426-1429.

Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.

Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.

Brincat SL, Miller EK. Frequency-specific hippocampal-prefrontal interactions during associative learning. Nat Neurosci. Apr. 2015; 18(4): pp. 576-581.

McNamara CG, Tejero-Cantero A, Trouche S, Campo-Urriza N, Dupret D. Dopaminergic neurons promote hippocampal reactivation and spatial memory persistence. Nat Neurosci. Dec. 2014// print; 17(12): pp. 1658-1660.

Ji D, Wilson MA. Coordinated memory replay in the visual cortex and hippocampus during sleep. Nat Neurosci. 2007; 10(1): pp. 100-107.

Kali S, Dayan P. Off-line replay maintains declarative memories in a model of hippocampal-neocortical interactions. Nat Neurosci. 2004; 7(3): pp. 286-294.

Rolls ET. Hippocampo-cortical and cortico-cortical backprojections. Hippocampus. 2000; 10: pp. 380-388.

Creutzfeldt OD, Fromm GH, Kapp H. Influence of transcortical d-c currents on cortical neuronal activity. Exp Neurol. Jun. 1962; 5: pp. 436-452.

Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.

Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.

Fröhlich F, McCormick DA. Endogenous electric fields may guide neocortical network activity. Neuron. Jul. 15, 2010; 67(1): pp. 129-143..

Ngo, H. V. V., Martinetz, T., Born, J., & Mölle, M. (2013). Auditory closed-loop stimulation of the sleep slow oscillation enhances memory. Neuron, 78(3), pp. 545-553.

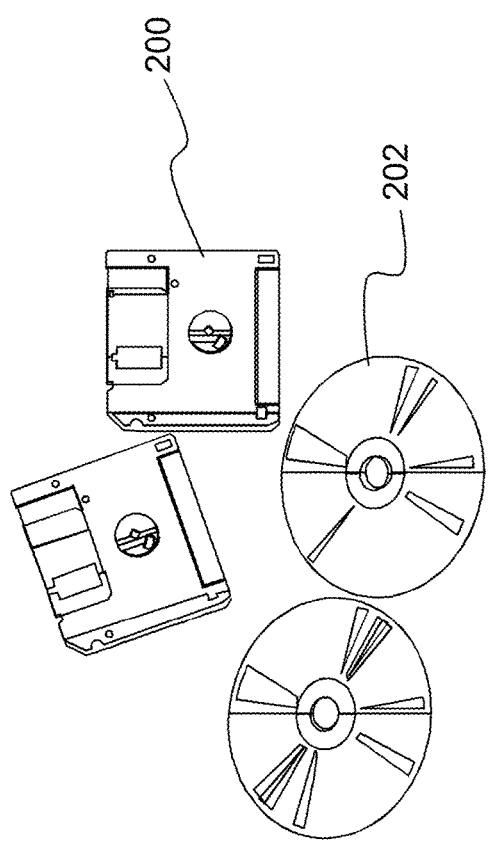

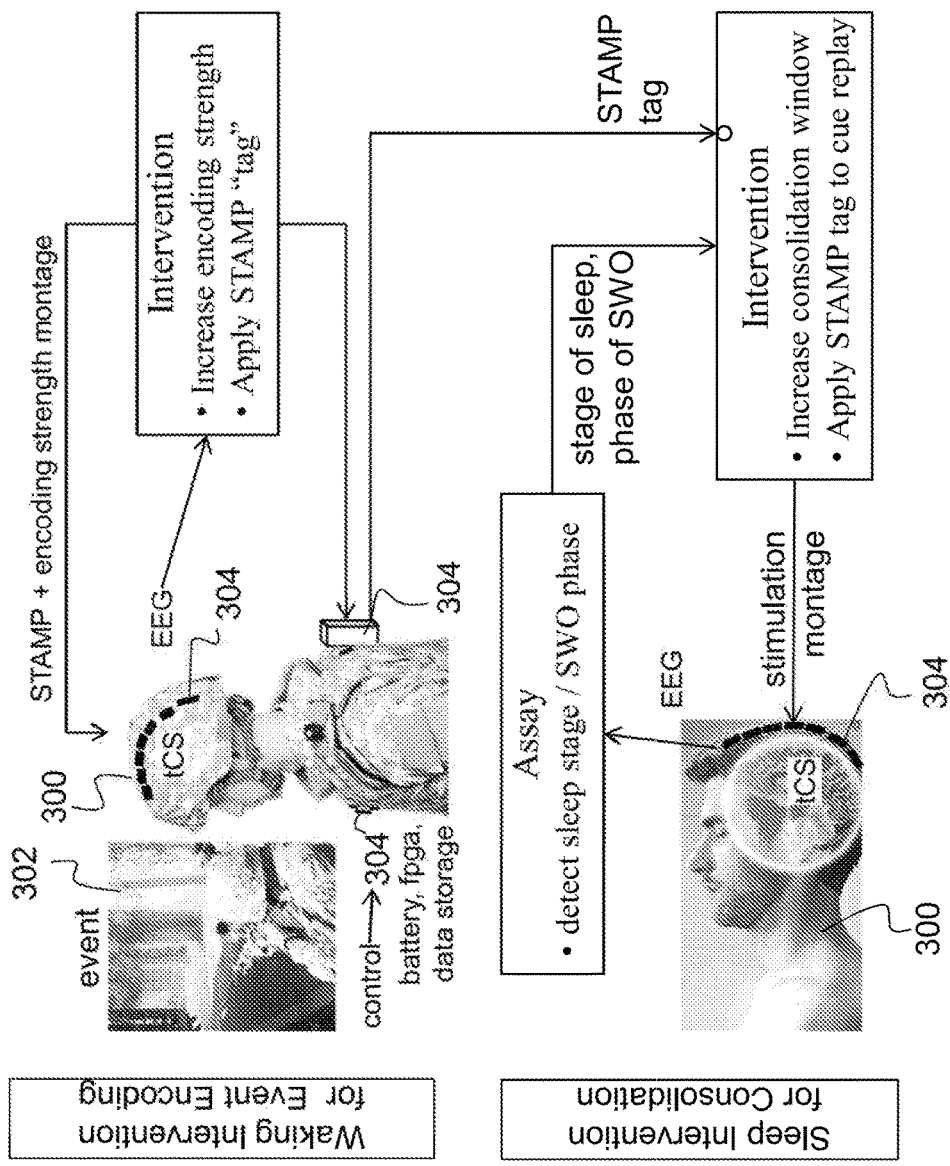
FIG. 3A  Waking Intervention for Event Encoding
FIG. 3B  Sleep Intervention for Consolidation Enhance encoding later Record during live event

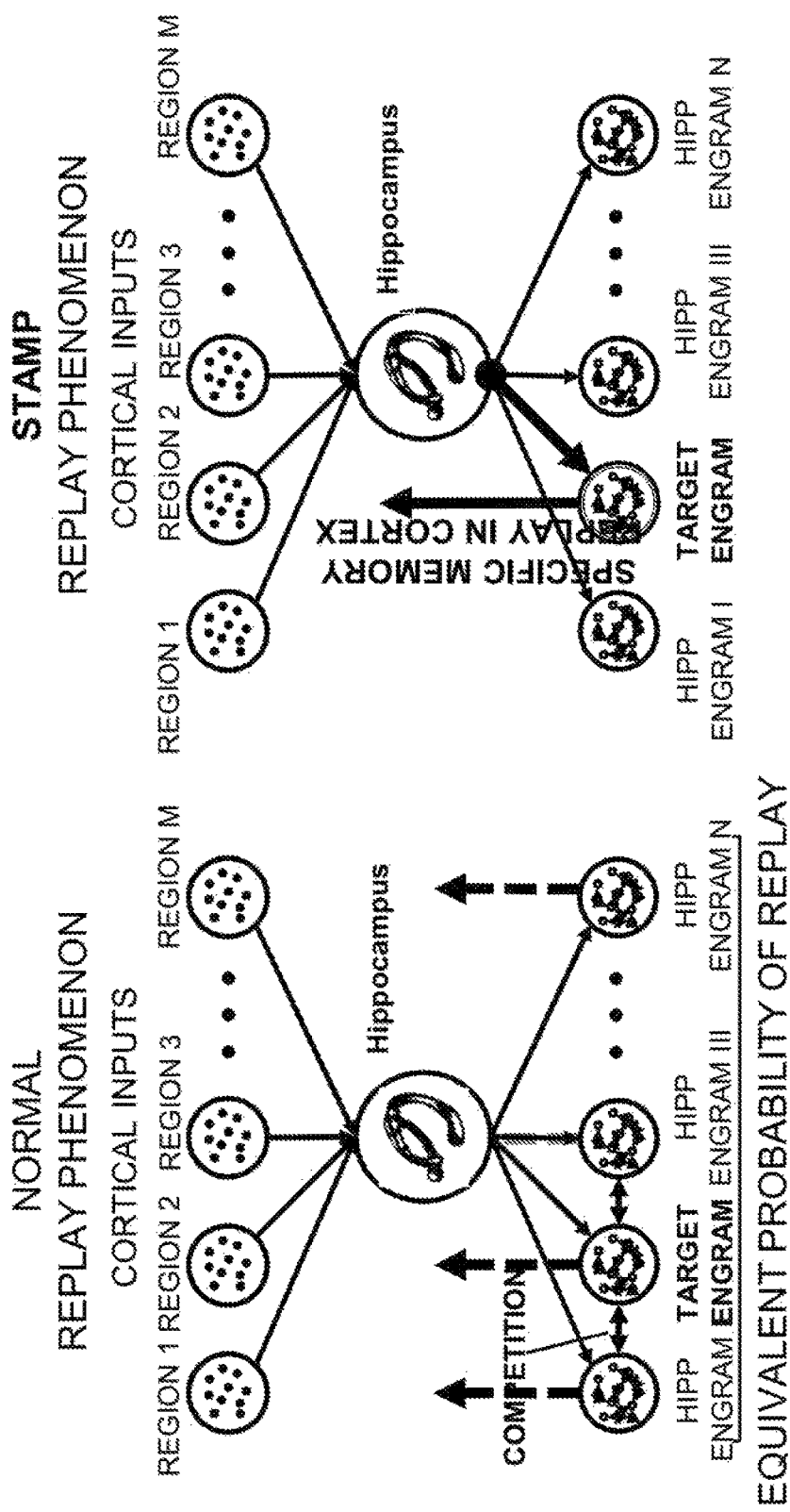

Key innovations and benefits compared to the state of the art (SOA).

| Innovations | Benefits Compared to SOA |
|---|---|
| Neurostimulation Learning Intervention applies tDCS of PFC to enhance replay probability, together with a unique SpatioTemporal Amplitude-Modulated Pattern (STAMP) of HD-tCS to "tag" specific experiences | • Produces specific replays (drugs cannot)<br>• STAMP tag does not need to compete with ambient environmental cues, and many more unique patterns are possible.<br>• tDCS on PFC strengthens encoding of a specific memory to boost subsequent replay incidence. |
| Neurostimulation Offline Intervention:<br>• Enhances and prolongs consolidation windows with closed-loop slow tACS (0.5-1.2 Hz) to PFC during NREM sleep (including slow wave sleep), and quiet waking<br>• STAMP tag induces specific replays | • Uses a single modality (tCS) to both enhance consolidation windows and provide cues that stimulate replay.<br>• Integrate a prior-art technique to slow the decay of SWS thereby enhancing the length of consolidation windows, by applying slow closed-loop tACS to PFC during NREM sleep (including slow wave sleep). |

| Hardware | Size | Weight | Power |
|---|---|---|---|
| Neuroelectrics 32-channel HD-tCS | 60 x 85 x 20 mm | 86 g | 15 V battery, ~8 hrs |
| Biosemi 64-channel HD-EEG | 120 x 150 x 190 mm | 1100 g | 4 W, >5 hrs |
| ANT-Neuro 64-channel HD-EEG | 160 x 205 x 22 mm | <500 g | battery, ~5 hrs |
| EGI integrated 128-ch HD-EEG/tCS | 101 x 280 x 280 mm | 4000 g | 12 V DC battery, 4-8 hrs |

METHOD AND SYSTEM TO ACCELERATE CONSOLIDATION OF SPECIFIC MEMORIES USING TRANSCRANIAL STIMULATION

GOVERNMENT LICENSE RIGHTS

This invention was made with government support under U.S. Government Contract Number N66001-14-C-4066. The government has certain rights in the invention.

CROSS-REFERENCE TO RELATED APPLICATIONS

This is a Non-Provisional patent application of 62/245,730, filed in the United States on Oct. 23, 2015, entitled, "Method and System to Accelerate Consolidation of Specific Memories Using Transcranial Stimulation," the entirety of which is hereby incorporated by reference.

BACKGROUND OF INVENTION

(1) Field of Invention

The present invention relates to a system for accelerated consolidation of specific memories and, more particularly, to a system for accelerated consolidation of specific memories using high-definition transcranial current stimulation (HD-tCS).

(2) Description of Related Art

In operational tasks, such as business and educational scenarios, it can be critically important to quickly integrate and accurately recall based on limited exposure to information. In state-of-the-art laboratory experiments, auditory or olfactory cues are associated with toy tasks during performance, and these cues are then used during sleep to trigger replays of that task performance memory (see the List of Incorporated Literature References, see Literature Reference Nos. 2, 3, and 6). However, these cues are impractical for operational use, because they can be lost in the complex ambient environment, and there are limited numbers of such cues that are uniquely discriminable. Additionally, drugs are also used in the prior art (see Literature Reference Nos. 4 and 5), but they cannot selectively enhance a particular memory.

Thus, a continuing need exists for a system for memory consolidation that is selective and will not degrade task performance or distract attention from learning the task.

SUMMARY OF INVENTION

The present invention relates to a system for accelerated consolidation of specific memories and, more particularly, to a system for accelerated consolidation of specific memories using high-definition transcranial current stimulation (HD-tCS). The system comprises a high-definition transcranial current stimulation (HD-tCS) system; a high-density electroencephalogram (HD-EEG) device for generating neural recordings from a subject; a sleep state detector for assessing the subject's sleep state from the neural recordings, and one or more processors and a non-transitory computer-readable medium having executable instructions encoded thereon such that when executed, the one or more processors perform an operation of generating a spatiotemporal amplitude-modulated pattern (STAMP) tag. During a memory encoding phase, the HD-tCS system simultaneously applies the STAMP tag and a transcranial direct current stimulation (tDCS) signal to the subject as an event is experienced by the subject. During a memory consolidation phase, the HD-tCS system applies a transcranial alternating current stimulation (tACS) signal to the subject during a sleep or quiet waking state of the subject.

In another aspect, the STAMP tag is a weighted combination of endogenous brain rhythms.

In another aspect, the HD-tCS system applies the STAMP tag during a sleep or quiet waking state of the subject to stimulate replays of a memory of the event and promote consolidation of the memory into the subject's long-term memory.

In another aspect, when a slow-wave-sleep (SWS) state is detected, the sleep state detector signals the HD-tCS system to apply a temporally compressed version of the STAMP tag to the subject.

In another aspect, the HD-tCS system applies the tACS signal when the sleep state detector detects non-rapid eye movement (NREM) sleep.

In another aspect, the event can be re-encoded in the memory of the subject by deliberate recall using a video of the event.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where:

FIG. 2 is an illustration of a computer program product according to some embodiments of the present disclosure;

FIG. 3A is an illustration of event encoding according to some embodiments of the present disclosure;

FIG. 3B is an illustration of memory consolidation according to some embodiments of the present disclosure;

FIG. 7C is an illustration of normal replay phenomenon according to some embodiments of the present disclosure;

FIG. 7D is an illustration of STAMP replay phenomenon according to some embodiments of the present disclosure;

FIG. 9 is a table illustrating innovations and benefits of embodiments of the present disclosure compared to the state-of-the-art; and FIG. 10 is a table illustrating currently available hardware that can be combined in multiple configurations according to some embodiments of the present disclosure.

DETAILED DESCRIPTION

Figure 1:
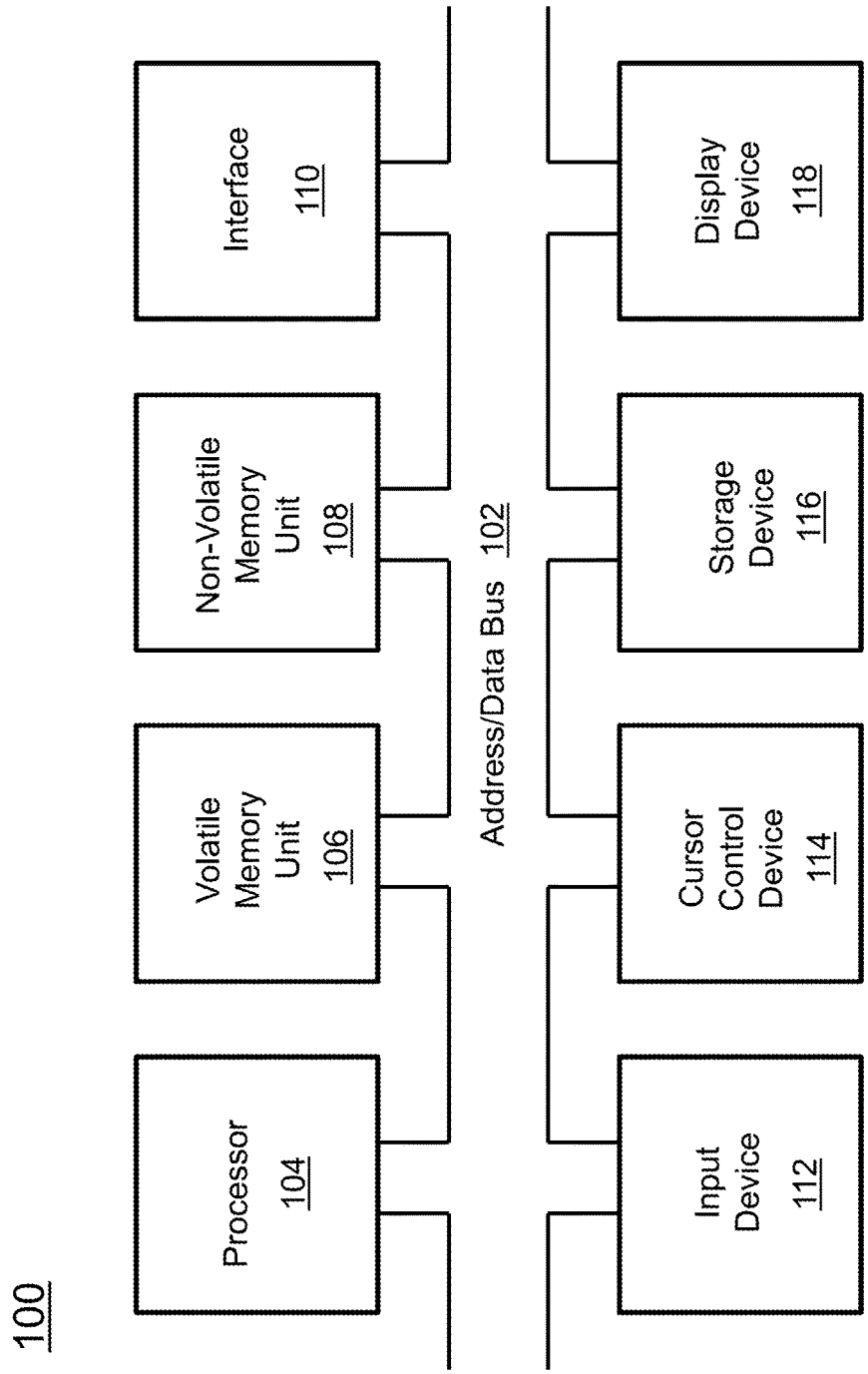
FIG. 1 is a block diagram depicting the components of a system for accelerated memory consolidation according to some embodiments of the present disclosure.

The present invention relates to a system for accelerated consolidation of specific memories and, more particularly, to a system for accelerated consolidation of specific memories using high-definition transcranial current stimulation (HD-tCS).

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number.

1. Marshall L, Helgadóttir H, Mölle M, Born J. Boosting slow oscillations during sleep potentiates memory. Nature. 2006; 444(7119):610-3.
2. Rudoy J D, Voss J L, Westerberg C E, Paller K A. Strengthening Individual Memories by Reactivating Them During Sleep. Science. 2009 Nov. 20; 326(5956): 1079-1079.
3. Diekelmann S, Biggel S, Rasch B, Born J. Offline consolidation of memory varies with time in slow wave sleep and can be accelerated by cuing memory reactivations. Neurobiol Learn Mem. 2012 September; 98(2):103-11.
4. Rasch B H, Born J, Gais S. Combined blockade of cholinergic receptors shifts the brain from stimulus encoding to memory consolidation. J Cogn Neurosci. 2006 May; 18(5):793-802.
5. Gais S, Born J. Low acetylcholine during slow-wave sleep is critical for declarative memory consolidation. Proc Natl Acad Sci USA. 2004 Feb. 17; 101(7):2140-4.
6. Rasch B, Buchel C, Gais S, Born J. Odor cues during slow-wave sleep prompt declarative memory consolidation. Science. 2007; 315(5817):1426-9.
7. Kirov R, Weiss C, Siebner H R, Born J, Marshall L. Slow oscillation electrical brain stimulation during waking promotes EEG theta activity and memory encoding. Proc. Natl. Acad. Sci. 2009; 106:15460-5.
8. Jutras M J, Fries P, Buffalo E A. Oscillatory activity in the monkey hippocampus during visual exploration and memory formation. Proc Natl Acad Sci. 2013 Aug. 6; 110(32):13144-9.
9. Brincat S L, Miller E K. Frequency-specific hippocampal-prefrontal interactions during associative learning. Nat Neurosci. 2015 April; 18(4):576-81.
10. McNamara C G, Tejero-Cantero A, Trouche S, Campo-Urriza N, Dupret D. Dopaminergic neurons promote hippocampal reactivation and spatial memory persistence. Nat Neurosci. 2014 12//print; 17(12):1658-60.
11. Ji D, Wilson M A. Coordinated memory replay in the visual cortex and hippocampus during sleep. Nat Neurosci. 2007; 10(1):100-7.
12. Kali S, Dayan P. Off-line replay maintains declarative memories in a model of hippocampal-neocortical interactions. Nat Neurosci. 2004; 7(3):286-94.
13. Rolls E T. Hippocampo-cortical and cortico-cortical backprojections. Hippocampus. 2000; 10:380-8.
14. Creutzfeldt O D, Fromm G H, Kapp H. Influence of transcortical d-c currents on cortical neuronal activity. Exp Neurol. 1962 June; 5:436-52.
15. Sederberg P B, Kahana M J, Howard M W, Donner E J, Madsen J R. Theta and gamma oscillations during encoding predict subsequent recall. J Neurosci Off J Soc Neurosci. 2003 Nov. 26; 23(34):10809-14.
16. Osipova D, Takashima A, Oostenveld R, Fernandez G, Maris E, Jensen O. Theta and gamma oscillations predict encoding and retrieval of declarative memory. J Neurosci. 2006; 26(28):7523-31.
17. Fröblich F, McCormick D A. Endogenous electric fields may guide neocortical network activity. Neuron. 2010 Jul. 15; 67(1):129-43.

18. Ngo, H. V. V., Martinetz, T., Born, J., & M611e, M. (2013). Auditory closed-loop stimulation of the sleep slow oscillation enhances memory. Neuron, 78(3), 545-553.

(2) Principal Aspects

Various embodiments of the invention include three "principal" aspects. The first is a system for accelerating memory consolidation. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

In operational tasks (as in many business and educational scenarios), it can be critically important to quickly integrate and accurately recall based on limited exposure to information. The invention described herein promotes memory consolidation to make this possible. It is based on the well-supported idea that when people sleep, the memory system "replays" memories, meaning they are recalled from short-term hippocampal memory and conveyed to the slower-learning cortical structures where they are slowly integrated non-destructively into a person's long-term memory store. Although any memory in hippocampus has a chance of being replayed during sleep, there is a greater probability that a specific memory will be replayed if it was recently learned and related to some emotional content or high immediate reward. Unfortunately, many things that need to be learned are boring or tedious, and the reward for learning them may be long delayed.

The system according to embodiments of the present disclosure combines a two-phase approach that is safe, non-invasive, and goes beyond the state-of-the-art (SOA). The memory to be consolidated is tagged by associating it with a cue. However, instead of audio or odor, the system applies a unique high-definition transcranial stimulation (HD-tCS) montage comprising a Spatio-Temporal Amplitude-Modulated Pattern (STAMP) of currents over sensory and association cortical sites during a distinct experience or skill learning. In general, STAMP can be any spatial, temporal, or spatiotemporal patterns of transcranial currents across the scalp over multiple channels. The STAMP tag is then applied later offline periods during quiet waking or slow-wave sleep (specifically during cortical UP states, which are brief alternating periods with high cortical activity) to cue the specific memory with which it was associated. The STAMP method according to embodiments of the present disclosure has the advantage that it will not degrade task performance or distract attention from learning the task.

STAMP is a unique technique that replaces the odor and audio tags previously described that have to compete with ambient environmental cues (see Literature Reference Nos. 2 and 6 for a description of odor and audio tags). STAMP tagging does not need to compete with ambient noise or smells, and many more unique patterns are possible with STAMP. Additionally, transcranial direct-current stimulation (tDCS) is applied to prefrontal cortex (PFC) during specific encoding to strengthen memory formation and boost subsequent replay likelihood and fidelity.

The invention described herein is a useful and non-intuitive approach with distinct advantages. While prior art has focused on laboratory research, real-world applications have not been considered. Therefore, the practicality of generating a unique tag based on sound or odors and producing it in a real-world environment (work, battlefield, school) has never been questioned. Equipment that is practical to produce electrical brain stimulation in a real-world environment has only recently become available (e.g., the EGI system listed in the table 1100 of FIG. 11). The prior art techniques that have been integrated into the system and method described herein have only been tested in the laboratory separately, never in combination with any other techniques for memory consolidation.

The system according to embodiments of the present disclosure accelerates consolidation of specific memories (e.g., items that the user needs to learn quickly and remember clearly and easily). The method will achieve 3× improved memory retention over a 48-hour period compared to SOA techniques (see Literature Reference Nos. 1-3 and 6) in tasks, such as recalling event sequences, making use of learned operational rules, and acquiring skills.

Significantly, this disclosure is the first description of employing distributed high-density electroencephalogram (HD-EEG) sensing and high-definition transcranial current stimulation (HD-tCS) in humans for unprecedented control over specific memory "replays" that consolidate those specific memories into long-term memory (see the table 900 in FIG. 9). In particular, this is the first description of application of a "STAMP" tag online as the event is experienced, so that the STAMP tag becomes associated with the event and can be used as a cue during sleep to cause the event to be recalled from memory.

STAMP is a weighted spatiotemporal function, and could be naturally instantiated using several endogenous brain rhythms (at theta, slow gamma, and fast gamma frequencies) that typically occur during attentive task performance across the brain, among others. HD-tCS applies the STAMP across the scalp. Further, tDCS is used on the PFC during the experience of the event to enhance the encoding strength as a means to enhance memory replay probability during subsequent offline periods. In addition, the approach according to various embodiments of the present disclosure is agnostic to stimulation technology and may be implemented through transcranial magnetic stimulation (TMS) as well. Further, electromagnetic STAMPs can be combined with unique sensory cues to further achieve unprecedented levels of targeted memory tagging and cueing. Finally, the system can be implemented using current commercially available technologies (e.g., Neuroelectrics 32-channel HD-tCS/EEG; Biosemi 64-channel HD-EEG; ANT Neuro 64-channel HD-EEG; EGI 128-channel HD-tCS/EEG) and may be integrated into man-portable systems.

In addition to the STAMP tag, two techniques have been integrated into the system described herein that are uniquely compatible with the STAMP, because they can be applied using an HD-tCS system. During learning, the system described herein applies tDCS to the PFC, causing local and distributed neural effects that have previously been correlated with strong memory formation (see Literature Reference Nos. 8 and 9). This manipulation increases subsequent offline replay fidelity of the specific memory (see Literature Reference No. 10). Furthermore, during NREM sleep or quiet waking transcranial alternating current stimulation (tACS)) at ongoing slow wave oscillation frequency and phase (closed-loop) is applied to PFC to enhance and prolong consolidation rhythms (as described in Literature Reference No. 1) for increasing the number of replays of the specific memory. This combination of interventions will dramatically boost memory retention on specific memories and skills by 3× over SOA because of the combined effects of increased encoding strength, increased replay probability of the specific memory, and broader consolidation windows.

The approach according to embodiments of the present disclosure can improve recall even if the event to be remembered is not anticipated in advance. Events can be re-encoded by deliberate recall with the help of video from a body camera. tDCS of the PFC and HD-tCS using a unique STAMP can then be applied during the re-encoding period. Certain drugs are used in prior art to encourage consolidation (see Literature Reference Nos. 4 and 5), but they are indiscriminate and can also have undesirable systemic side effects.

The invention described herein will improve consolidation of specific memories (i.e., the "event"). FIGS. 3A and 3B illustrate that a two-part intervention enhances memory during both waking (FIG. 3A) and sleep (FIG. 3B). When awake (FIG. 3A), the stimulation (e.g., tCS) of the user 300 enhances memory encoding and at the same time applies a STAMP "tag". When the user 300 is asleep, the intervention enhances the consolidation window while also encouraging specific memory replays. SWO denotes slow wave oscillation.

In one embodiment, when the event 302 is first experienced (e.g., when the user 300 is learning something new (such as a set of operational rules or facts, or experiencing an episode on the field that has to be debriefed later), he/she wears an intervention system 304 consisting of a combined array of HD-EEG sensors and HD-tCS stimulating electrodes (FIG. 3A). Note that although the embodiment is described in terms of H D-tCS, one skilled in the art can readily implement the same approach using transcranial magnetic stimulation (TMS), or other methods of changing the single unit firing rates and local field potentials (LFPs) in selected regions of the brain.

The table 1000 in FIG. 10 shows that the EGI system already provides such a system. The table 1000 lists currently available hardware that can be combined in three configurations, all of which are man-portable.

A simple computing device is included in the intervention system 304 to compute the STAMP tag (e.g., a field-programmable gate array (FPGA)), and a data storage drive is included in the intervention system 304 to record the computed STAMP tag for later use to cue the memory. This STAMP tag is applied in a HD-tCS montage, together with a different montage (for focal tDCS of the PFC) that increases encoding strength.

Later, during sleep or quiet waking, as depicted in FIG. 3B, the user 300 again wears the intervention system 304, which detects the stage of sleep and applies the STAMP tag to cue the memory during transcranially sensed positive ("UP") phases of slow-wave sleep (SWS) to stimulate replays of that specific memory. This is applied together with another stimulation montage that enhances the duration and robustness of the consolidation window. These operations are described in further detail below.

Figure 4B:
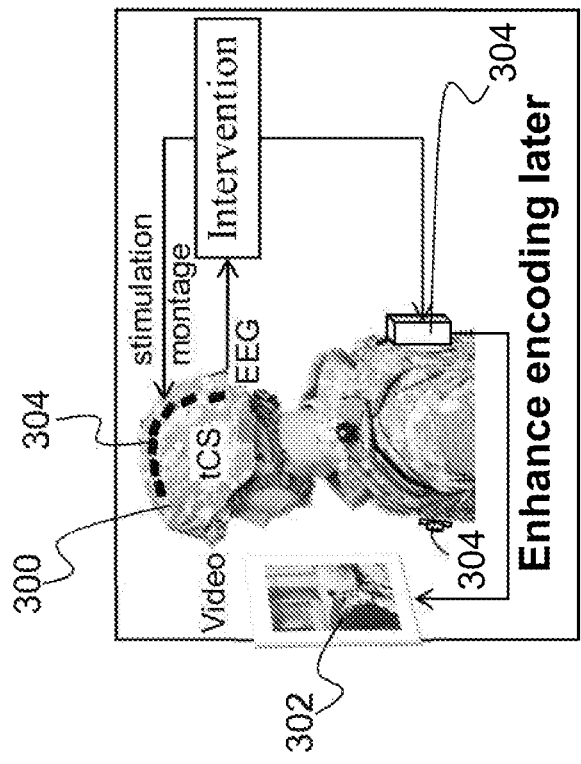
FIG. 4B is an illustration of enhancing encoding of an event at a later time according to some embodiments of the present disclosure.
Figure 4A:
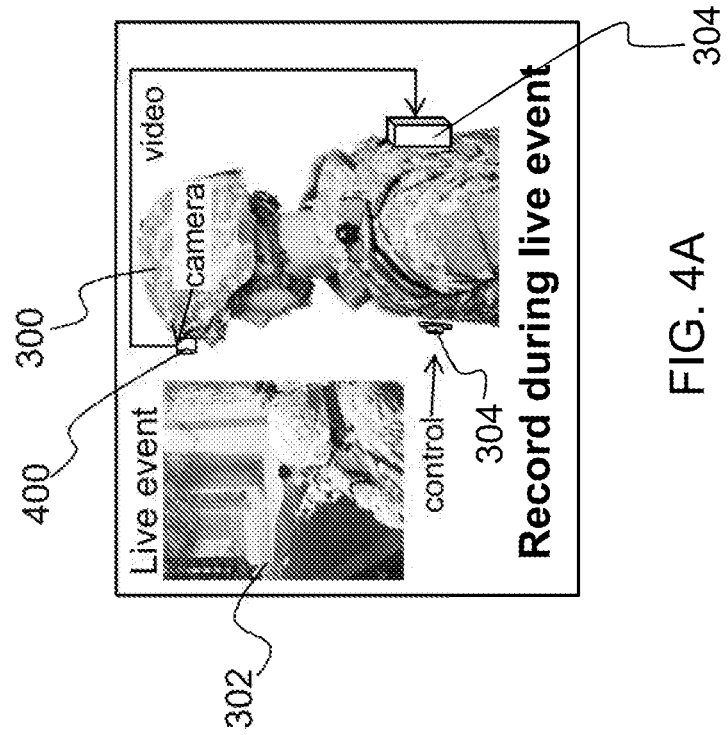
FIG. 4A is an illustration of recording during a live event according to some embodiments of the present disclosure.

Another embodiment of the invention is shown in FIGS. 4A and 4B. As depicted, the waking interventions can also be applied after an event 302 has occurred by allowing a user 300 to relive the event 302 in their imagination or by watching video recorded from wearable cameras 400. In this embodiment, when the event 302 occurs (i.e., a live event which is recorded), the user 300 does not have the intervention system 304 handy (FIG. 4A). In this case, the user 300 must perform the encoding step (depicted in FIG. 3A) at a later time, while reliving the event 302 as clearly as possible (FIG. 4B). This can be facilitated more effectively if the user 300 wore a camera 400 during the event 302, and can review the video later to refresh the memory. The sleep intervention operations depicted in FIG. 3B can then be performed normally.

Figure 5A:
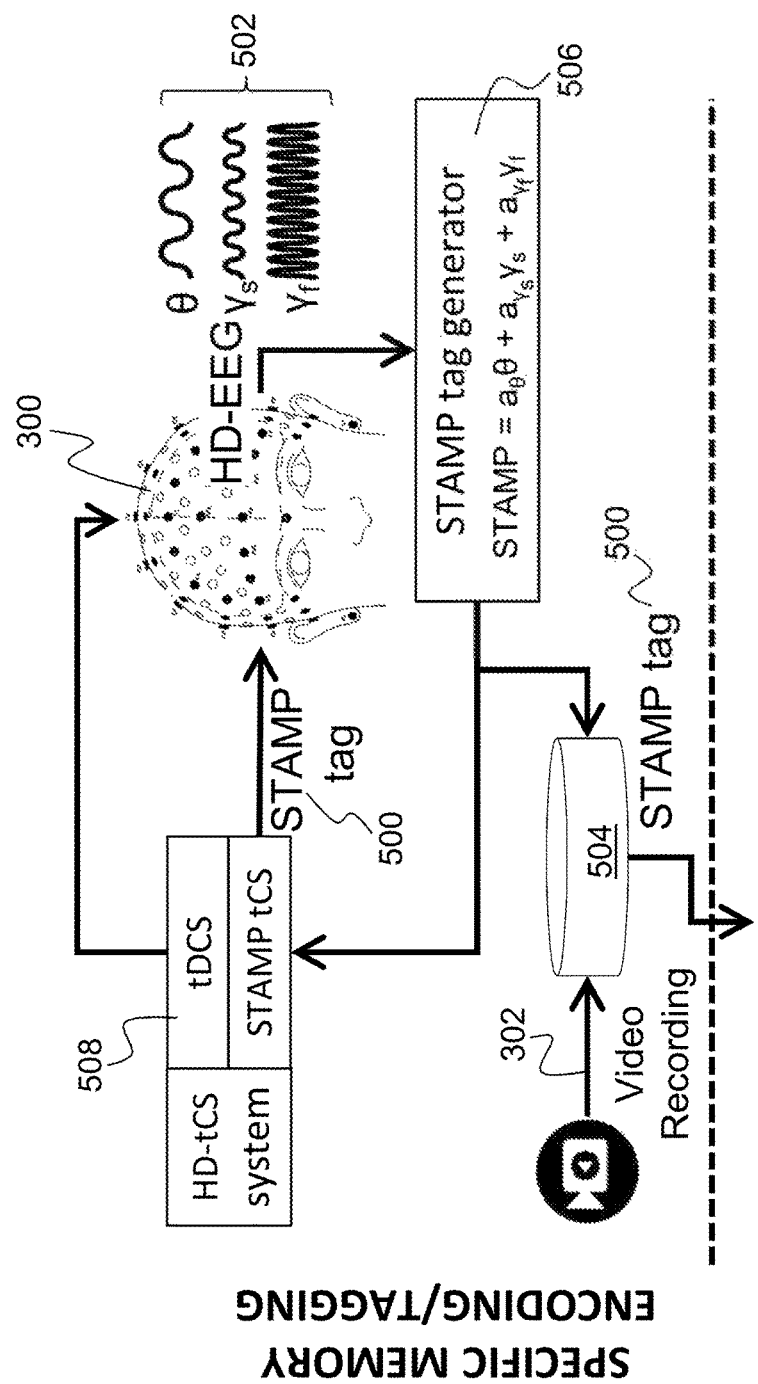
FIG. 5A is an illustration of memory encoding/tagging according to some embodiments of the present disclosure.
Figure 5B:
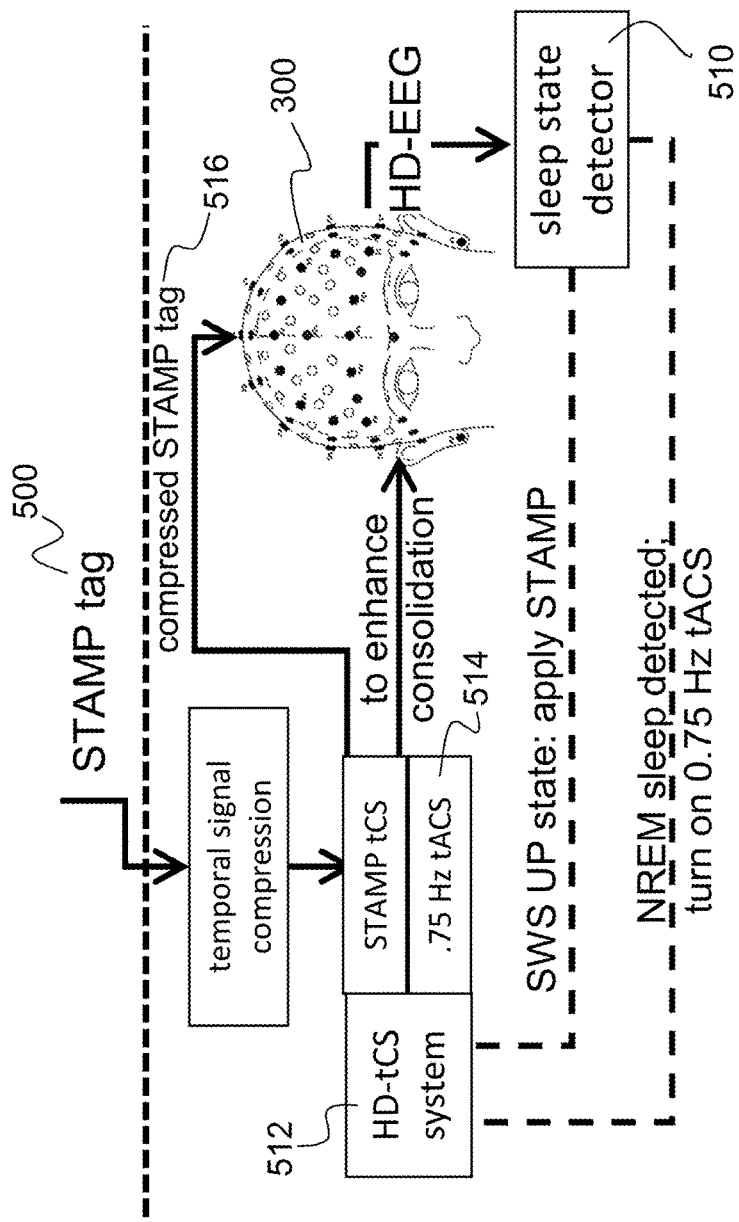
FIG. 5B is an illustration of memory consolidation according to some embodiments of the present disclosure.

FIGS. 5A and 5B illustrate the two phases of operation in more detail. As in FIGS. 3A and 3B, FIG. 5A depicts how the system is used during encoding, and FIG. 5B depicts how it is used during memory consolidation (sleep or quiet waking). The STAMP tag 500 is a weighted function of several endogenous brain rhythms 502 recorded (via, for instance, HD-EEG) during the experience of the event in one instantiation. Slow and fast gamma frequencies and theta frequency are shown because of their association with encoding and retrieval of declarative memories (such as described in Literature Reference Nos. 8, 9, 15, and 16), but other frequencies (e.g., beta frequencies) may also be utilized due to their relationship with active concentration.

The STAMP tag 500 is immediately applied to the brain of the user 300 using electrical stimulation (e.g., HD-tCS, tDCS) and is also stored (in a data storage drive 504). The STAMP equation 506 shown in FIG. 5A incorporates slow and fast gamma as well as theta frequencies (known a priori), but could also incorporate beta frequencies, which are associated with active concentration. The cumulative mean amplitude of the STAMP across the scalp, in one embodiment, will be about 2 milliamperes (mA). One skilled in the art could experiment with different values to find the optimal STAMP that is strong enough to "tag" the memory without overly influencing it. Concurrent with the application of the STAMP tag 500, maximum intensity or maximum focality tDCS 508 is applied to the PFC only, which has the effect of improving the strength of the encoded memory and, thereby, the probability that the particular memory will be replayed during subsequent offline periods. Here, maximum intensity or focality refer to tCS electrode placements that are optimized to induce either maximally intense or maximally focal electric fields or current flows at a specified location, respectively.

FIG. 5B shows the memory consolidation phase of the intervention, in which a sleep state detector 510 (commonly available commercially) detects when NREM (non-rapid-eye-movement sleep) begins. This event causes the HD-tCS system 512 to begin applying a closed-loop slow tACS montage 514 on the PFC with returns on mastoids or other appropriate location, enhancing the consolidation window by lowering the decay rate of SWS (slow wave sleep) cycles. Each time a SWS UP state is detected (i.e., the positive part of the slow-wave oscillation), the sleep state detector 510 signals the HD-tCS system 512 to apply a temporally compressed version of the STAMP tag 516. The temporally compressed version of the STAMP tag 516 is compressed to a higher frequency (i.e., cortical replay speeds) for the application during offline periods. For purely spatial STAMP (namely, STAMP tDCS), temporal compression doesn't apply. One implementation of embodiments of the present disclosure is to compress the signal to a cortical replay speed of 10× the real-time STAMP rate, but one skilled in the art might experiment with this rate. Depending on the individual subject and the type of memory, this compression factor might be different.

Detection of SWS UP states is known to those skilled in the art (see, for example, Literature Reference No. 18). As an alternative, if it is not possible to detect UP states due to sensing limitations, the STAMP intervention can be applied periodically as was done in SOA; for example, every 5 seconds for the duration of SWS during NREM sleep, as described in Literature Reference No. 2.

Figure 6:
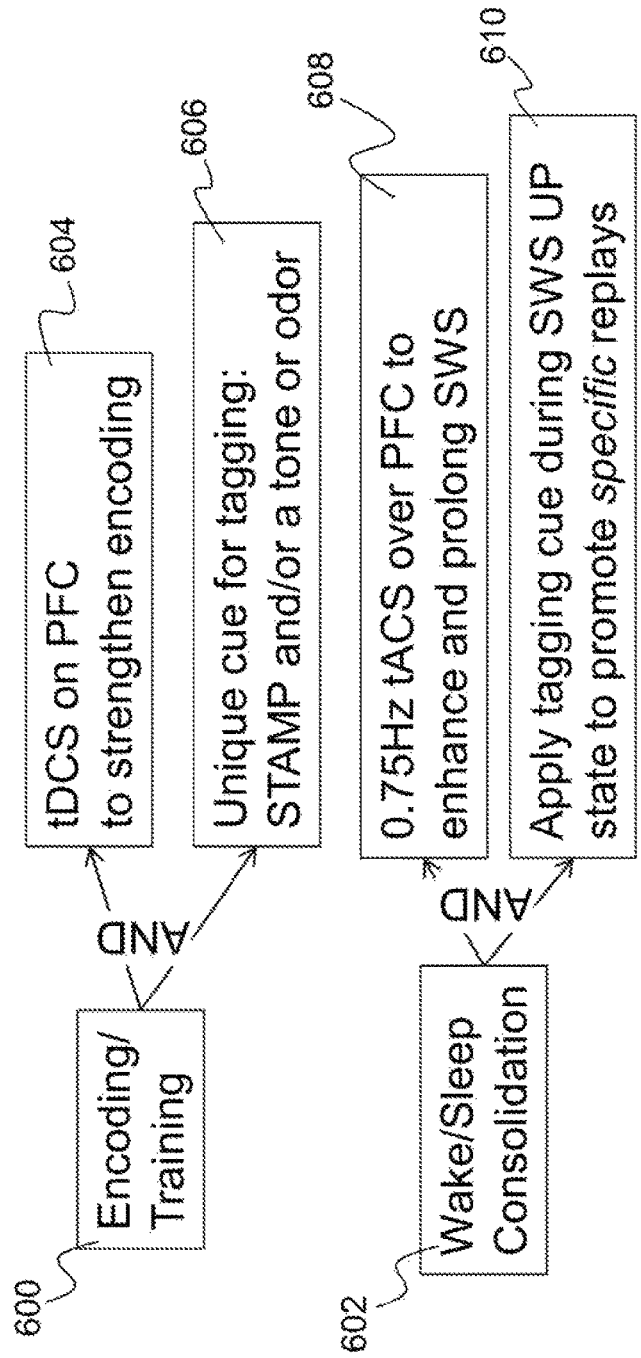
FIG. 6 is an illustration of the two-stage intervention plan according to some embodiments of the present disclosure.

FIG. 6 illustrates how the different interventions are combined during encoding and consolidation phases of use. Our two-stage intervention plan integrates a set of complementary interventions to be applied during an encoding/training phase 600 and also during a wake/sleep consolidation phase 602. As described above, during the encoding/training phase 600, tDCS stimulates the PFC to strengthen encoding (element 604), and a unique tag (e.g., STAMP, tone, odor) is used (element 606). In the wake/sleep consolidation phase 602, tACS is used to stimulate the PFC to enhance and prolong SWS (element 608), and the tagging cue is applied during an SWS UP state to promote specific replays (element 610).

(3.1) Theory and Technical Description of Technique

The intervention approach according to embodiments of the present disclosure is based on the theory of a bi-directional dialogue between the neocortex and the hippocampus (HC) during memory encoding and consolidation, as described in Literature Reference No. 11. Sparse distributed multi-modal neocortical representations selectively code sequences of events and/or actions, and drive the rapid encoding of corresponding memory engrams in the HC during wake.

Later during SWS, the neocortical cells exhibit non-specific synchronous activation. This synchronous activation establishes the initial conditions for the generation of hippocampal SWRs (standing wave ratios) and time-compressed replays of specific memories in the recurrent CA3 (*cormis ammonss* 3) network based on the strengths of their encoding. This then leads to a cascading effect in which the replayed sequence memories within the HC are sent back to the neocortex through hippocampal-neocortical back projections (see Literature Reference No. 13), where cells constituting the same sequential memory are primed to fire at higher levels during the SWS UP state. This mechanism, thus, drives the slow long-term consolidation of the most salient of the newly experienced events, or newly acquired skills, within the recurrent neocortical connections. This mechanism improves specific memory recall by biasing the typically non-specific firing of neocortical UP states during SWS to trigger such loops of coordinated hippocampal-neocortical replays.

The online encoding and offline consolidation processes offer the ideal entry points for targeted intervention to boost long-term memory retention in human subjects. The challenge is to be able to externally boost memory encoding as well as externally induce the replay of a particular memory, when there are several competing hippocampal engrams to be re-activated during SWS. To address this, a distributed high-density transcranial EEG (HD-EEG) sensing and high-definition transcranial current stimulation (HD-tCS) system is employed to gain significant control over the offline replays of specific memories.

As depicted in FIGS. 5A and 5B, the distributed neocortex is stimulated with a Spatio-Temporal Amplitude-Modulated Pattern (STAMP) of currents (based on endogenous rhythms in this example) during encoding of a selected memory to tag the memory, while simultaneously applying maximum intensity tDCS to PFC (to enhance encoding strength). Then, during sleep, the same STAMP montage is applied during transcranially assessed UP phases of slow-wave sleep in order to cue a replay of the specific memory of interest, while simultaneously applying slow closed-loop tACS to the PFC throughout NREM sleep and quiet waking periods (to enhance and prolong SWS). Extending the SWS duration increases the potential number of replays to affect consolidation, and has been directly correlated with reduced recall error in human subjects, as described in Literature Reference No. 3.

To address the concern that the approach described herein could interfere with, or disrupt, memory formation, it is important to note that the approach does not directly drive cells to supra-threshold firing, but results in slight changes to the membrane potential of individual cells located within the induced electric field (see Literature Reference No. 14). To date, there have been no reports of performance disruption arising from application of tACS. Therefore, modulation of endogenous rhythms using HD-tCS with similar frequencies, but with spatiotemporally distributed amplitudes, will not degrade task performance or distract attention.

STAMP should be applied to the high-level areas in the sensory cortical processing hierarchies; in particular, the temporal and parietal areas. Because of the integrative nature of these higher processing areas, they are closer to the entorhinal gateways for the inputs to and outputs from the HC.

The latest data from experimental studies that measure the effect of transcranial stimulation on specific brain regions by means of implanted electrode arrays shows that tDCS applied to the PFC results in strengthening the synchrony of local field potential (LFP) activity between cortical and hippocampal regions in various pertinent frequency bands. Synchronous neural activity at endogenous θ and γ frequencies has been associated with stronger memory formation (see Literature Reference No. 9). Transcranial stimulation data indicates that memory encoding can be strengthened by applying user-triggered tDCS to the PFC during desired memory encoding periods. This has the effect of increasing signal-to-noise ratio in the hippocampalcortical network and improved temporal coordination among the distributed brain areas involved in the memory system.

(3.2) STAMP Signal

The memory tagging approach according to embodiments of the present disclosure takes advantage of the known tACS-based entrainment (phase synchronization) of spiking activity in in vitro slice preparations, as described in Literature Reference No. 17. The STAMP signal would modulate the timing of spiking activity in the various neocortical inputs to the HC in a spatiotemporally distributed manner. In other words, the timing properties of the distributed cortical signals feeding a hippocampal engram can be reproducibly affected using HD-tCS with the memory-specific STAMP. Thus, the STAMP montage can tag the neocortical spiking activity of incoming streams to the HC with region-dependent phase synchrony modulation.

Figures 7A, 7B:
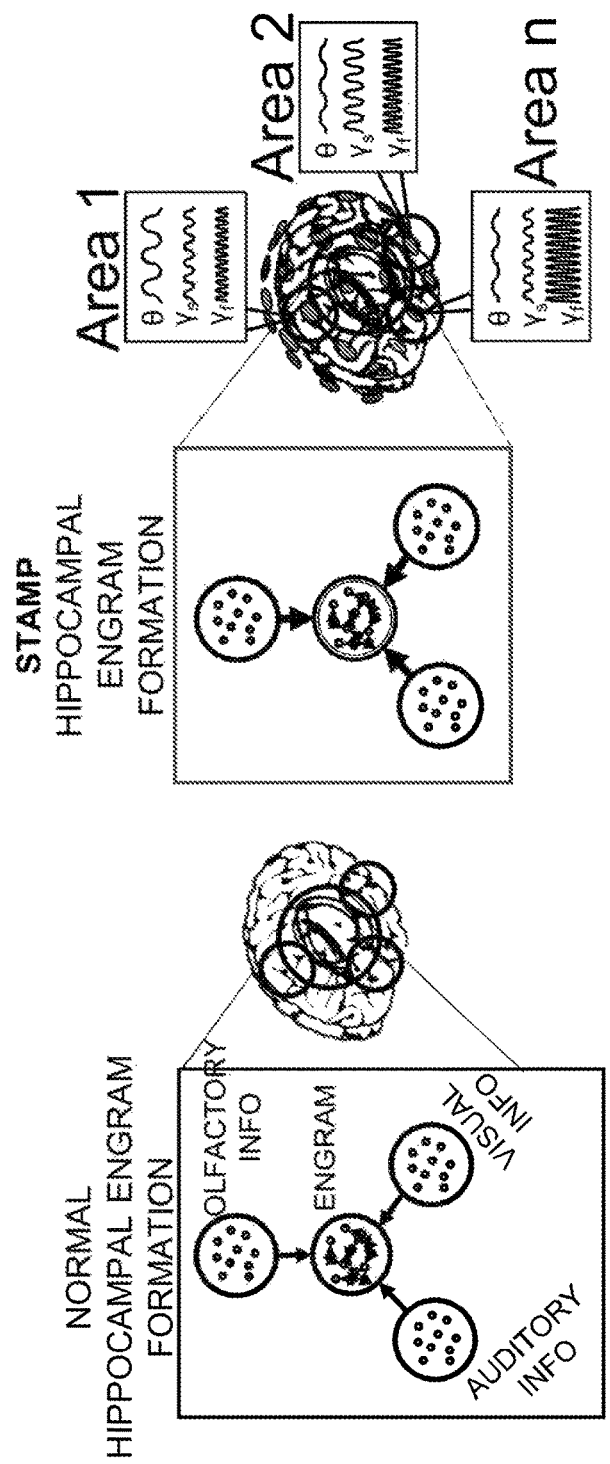
FIG. 7A is an illustration of normal hippocampal engram formation according to some embodiments of the present disclosure.
FIG. 7B is an illustration of spatio-temporal amplitude-modulated pattern (STAMP) engram formation according to some embodiments of the present disclosure.

FIG. 7A shows how different sensory aspects of a memory or skill performance, which are encoded by different cortical structures, are rapidly bound into an unified neural representation (called "engram") in the hippocampus. FIG. 7B depicts how the STAMP signal is used to "tag" the memory of interest by changing the spike-field coherence and phase synchrony of the cortical origins of information to the HC. FIG. 7C shows how different engrams of memories experienced or skills performed during the day or previous recent days have similar low probabilities to get reactivated in the hippocampus and cortex during sleep. During the consolidation phase (i.e., SWS UP states), STAMP is applied once more, re-establishing the distributed functional context within and between neocortical areas and the HC, preferentially re-activating the tagged memory over the other potentially replayable engrams in competition (see FIG. 7D). Variations in phase synchronization of distributed brain regions over multiple frequency bands underlie the enormous variety in distinctive sensory perceptions and cognitive behaviors. Therefore, the application of a unique STAMP during the encoding of a particular memory will have a substantially strong "priming" effect on the rapid binding process within the HC linking cortical inputs to the hippocampal engram. The cortical cells in the distributed high-level areas can also be phase synchronized during SWS UP states to a similar spatiotemporal pattern as that during memory encoding using the same STAMP stimulation. Because the bidirectional theory of memory replays posits that there exists competition among recently acquired salient hippocampal engrams to be replayed during SWS, such a modulation of the cortical inputs will substantially boost the probability to elicit the hippocampal engram of the STAMP-tagged event over other events.

The invention described herein will allow, for the first time, a targeted and personalized closed-loop system for enhancing memory in both normal subjects and those with learning difficulties related to memory consolidation. The system can be used for training, or as a commercial product. The interventions employing closed-loop HD-EEG sensing and HD-tCS stimulation can be incorporated into commercial products with appropriate licensing. Currently, available hardware is already in man-portable range for commercial applications (see FIG. 10). An integrated brain monitoring and transcranial stimulation system will have broad applicability in research and rehabilitation, and in new development of commercial and military applications.

Figure 8:
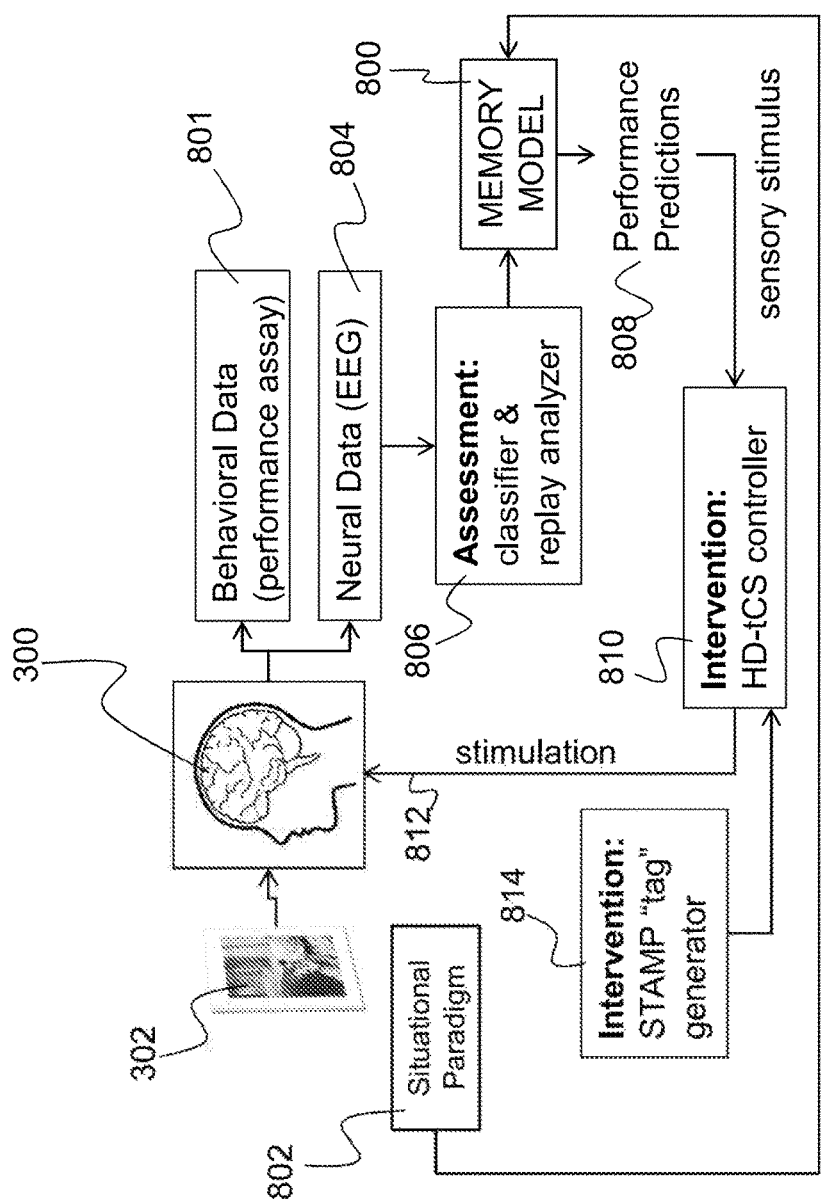
FIG. 8 is an illustration of the overall process for consolidating a memory according to some embodiments of the present disclosure.

FIG. 8 is an illustration of the end-to-end system that operates during both wake learning as well as sleep consolidation. A memory model 800 is personalized to the user's learning in response to sensory stimuli, or a situational paradigm 802, during waking from ongoing behavioral data 801, as well as brain and body signals (neural data 804), and adapts in response to the assessment or classification of replays or reactivations of spatiotemporal brain activity patterns corresponding to specific memories or skills (i.e., Assessment: classifier and replay analyzer 806). Online predictions of future performance of the user (i.e. performance predictions 808) on particular memories or skills of interest during sleep, as replays occur, control the scheduling, or intervention, of memory-specific stimulation (namely, STAMP) using HD-tCS controller (i.e., Intervention: HD-tCS controller 810) during cortical UP states to facilitate the preferential consolidation of weaker memories or skills first among the desired set through stimulation 812 of the user 300. Different unique memories or skills are tagged with different STAMPs (i.e., Intervention: STAMP "tag" generator 814).

Products resulting from the system according to embodiments of the present disclosure will enable people to reinforce episodic memories and acquire skills faster as they sleep. As an added benefit, the intervention described herein will increase overall cognitive alertness by promoting longer periods of SWS (or deep sleep). For instance, consider a user who would like to learn to play a particular complex sequence on a piano. The user or the teacher commands the system to generate a unique STAMP, which is then applied while the sequence is being executed or practiced. Also, the system applies tDCS of the prefrontal cortex (PFC) during learning to enhance memory formation or initial encoding to boost the probability of the desired sequences to be replayed during subsequent offline consolidation periods. At the same time as waking stimulation, EEG, ECG, EMG signals, and other brain and body signals from wearable sensors are recorded to enable the offline learning of spatiotemporal templates that are leveraged later to identify the replays of the sequence during quiet waking or slow-wave sleep. A personalized behavioral model is also instantiated for the user that adapts to sensory stimuli as well as biometrics of, for instance, stress, fatigue, and attention during waking, and also to classified replays of various memories during sleep. Online behavioral predictions in response to ongoing replay activity during sleep is used to schedule the application of STAMPs for the weaker memories among the desired set during cortical UP states in slow-wave sleep. The behavioral output following sleep is improved performance on each memory of interest, compared to the case where no intervention whatsoever is applied.

The augmentation technology and therapeutic procedure is safe and non-invasive; it does not require drugs or surgery. In addition, the system can be trained on an event that is identified by the subject either before the event happens, or sometime after it happens (in which case the user turns on the system as the event is recalled as clearly as possible). Further, the interventions are automatically applied during online memory encoding and subsequent offline memory consolidation, and do not require expert supervision or a clinical setting. The system applies targeted stimulation on the scalp only while learning, and later during slow-wave sleep cycles during quiet waking or sleep (about 20-40 minutes per night). Compared with a drug whose effects are dependent on pharmacokinetics and individual metabolisms, the approach described herein is more targeted and reliable.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for memory consolidation, the system comprising:
   a high-definition transcranial current stimulation (HD-tCS) system;
   a high-density electroencephalogram (HD-EEG) device for generating neural recordings;
   one or more processors and a non-transitory computer-readable medium having executable instructions encoded thereon such that when executed, the one or more processors perform an operation of generating a spatiotemporal amplitude-modulated pattern (STAMP) tag; and a sleep state detector for assessing the sleep state from the neural recordings, wherein during a memory encoding phase, the HD-tCS system simultaneously applies the STAMP tag and a transcranial direct current stimulation (tDCS) signal during an event, and wherein during a memory consolidation phase, the HD-tCS system applies a transcranial alternating current stimulation (tACS) signal during a sleep or quiet waking state.

2. The system as set forth in claim 1, wherein the STAMP tag is a weighted combination of endogenous brain rhythms.

3. The system as set forth in claim 1, wherein the HD-tCS system applies the STAMP tag during the sleep or quiet waking state to stimulate replays of a memory of the event and consolidate the memory.

4. The system as set forth in claim 1, wherein when a slow-wave-sleep (SWS) state is detected, the sleep state detector signals the HD-tCS system to apply a temporally compressed version of the STAMP tag.

5. The system as set forth in claim 1, wherein the HD-tCS system applies the tACS signal when the sleep state detector detects non-rapid eye movement (NREM) sleep.

6. The system as set forth in claim 1, wherein the event can be re-encoded in a memory by deliberate recall using a video of the event.

7. A method for memory consolidation, comprising acts of:

generating neural recordings using a high-density electroencephalogram (HD-EEG) device;

assessing the sleep state from the neural recordings using a sleep state detector;

generating a spatiotemporal amplitude-modulated pattern (STAMP) tag;

during a memory encoding phase, simultaneously applying, using a high-definition transcranial current stimulation (HD-tCS) system, the STAMP tag and a transcranial direct current stimulation (tDCS) signal during an event; and during a memory consolidation phase, applying, using the HD-tCS system, a transcranial alternating current stimulation (tACS) signal during a sleep or quiet waking state.

8. The method as set forth in claim 7, wherein the STAMP tag is a weighted combination of endogenous brain rhythms.

9. The method as set forth in claim 7, wherein the HD-tCS system applies the STAMP tag during the sleep or quiet waking state to stimulate replays of a memory of the event and consolidate the memory.

10. The method as set forth in claim 7, wherein when a slow-wave-sleep (SWS) state is detected, the sleep state detector signals the HD-tCS system to apply a temporally compressed version of the STAMP tag.

11. The method as set forth in claim 7, wherein the HD-tCS system applies the tACS signal when the sleep state detector detects non-rapid eye movement (NREM) sleep.

12. The method as set forth in claim 7, wherein the event can be re-encoded in the memory by deliberate recall using a video of the event.

13. A computer program product for memory consolidation, the computer program product comprising:

computer-readable instructions stored on a non-transitory computer-readable medium that are executable by a computer having one or more processors for causing the processor to perform operations of:

generating neural recordings using a high-density electroencephalogram (HD-EEG) device;

assessing the sleep state from the neural recordings using a sleep state detector;

generating a spatiotemporal amplitude-modulated pattern (STAMP) tag;

during a memory encoding phase, simultaneously applying, using a high-definition transcranial current stimulation (HD-tCS) system, the STAMP tag and a transcranial direct current stimulation (tDCS) signal during an event; and during a memory consolidation phase, applying, using the HD-tCS system, a transcranial alternating current stimulation (tACS) signal during a sleep or quiet waking state.

* * * * *